United States Patent
Leet

(10) Patent No.: US 6,228,352 B1
(45) Date of Patent: *May 8, 2001

(54) HAIR STYLING AGENTS AND COMPOSITIONS CONTAINING HYDROPHOBIC HAIR STYLING POLYMERS

(75) Inventor: Julia Elizabeth Leet, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/335,422

(22) Filed: Nov. 7, 1994

Related U.S. Application Data

(63) Continuation of application No. 08/156,655, filed on Nov. 22, 1993, now abandoned, which is a continuation of application No. 07/828,848, filed on Jan. 31, 1992, now abandoned, which is a continuation of application No. 07/712,026, filed on Jun. 7, 1991, now abandoned.

(51) Int. Cl.$^7$ ............................... A61K 7/06; A61K 7/11; A61K 6/00; A61K 7/00
(52) U.S. Cl. ..................... 424/70.16; 424/70.11; 424/70.12; 424/70.13; 424/70.27; 424/70.1; 424/401
(58) Field of Search .................. 424/70.11, 70.12, 424/70.13, 70.16, 401, 70.27, 70.1

(56) References Cited

U.S. PATENT DOCUMENTS

| | | |
|---|---|---|
| 3,395,041 | 7/1968 | Hsiung .................................. 132/7 |
| 3,579,632 | 5/1971 | Sonnen ................................. 424/70 |
| 3,723,325 | 3/1973 | Parran ................................. 252/106 |
| 4,228,277 | 10/1980 | Landoll ................................. 536/90 |
| 4,243,802 | 1/1981 | Landoll ................................. 536/91 |
| 4,331,167 | 5/1982 | Wajaroff ................................. 132/7 |
| 4,352,916 | 10/1982 | Landoll ................................ 526/200 |
| 4,374,825 | 2/1983 | Bolich, Jr. et al. .................... 424/70 |
| 4,421,740 | 12/1983 | Burton ................................. 424/70 |
| 4,435,217 | 3/1984 | House ................................. 106/171 |
| 4,459,285 | 7/1984 | Grollier et al. ....................... 424/74 |
| 4,465,517 | 8/1984 | Shields ................................ 106/35 |
| 4,485,089 | 11/1984 | Leipold ................................. 424/49 |
| 4,523,010 | 6/1985 | Lukach et al. ........................ 536/91 |
| 4,529,523 | 7/1985 | Landoll ........................... 252/8.55 D |
| 4,557,928 | 12/1985 | Glover ................................. 424/70 |
| 4,581,230 | 4/1986 | Grollier et al. ....................... 424/74 |
| 4,584,189 | 4/1986 | Leipold ................................. 424/54 |
| 4,610,874 | 9/1986 | Matravers ............................. 424/70 |
| 4,683,004 | 7/1987 | Goddard ............................. 106/170 |
| 4,684,704 | 8/1987 | Craig ................................. 526/200 |
| 4,707,189 | 11/1987 | Nickol ................................ 106/176 |
| 4,725,433 | 2/1988 | Matravers ............................. 424/70 |
| 4,826,970 | 5/1989 | Reid et al. ............................ 536/66 |
| 4,902,499 | 2/1990 | Bolich, Jr. et al. .................... 424/70 |
| 4,963,348 | 10/1990 | Bolich et al. .......................... 424/71 |
| 4,981,902 | 1/1991 | Mitra et al. .......................... 524/547 |
| 4,981,903 | 1/1991 | Garbe et al. .......................... 524/547 |
| 4,983,377 | 1/1991 | Murphy et al. ........................ 424/47 |
| 4,983,383 | * 1/1991 | Maksimoski ..................... 424/70.11 |
| 4,983,418 | 1/1991 | Murphy et al. ........................ 424/47 |
| 4,988,506 | 1/1991 | Mitra et al. ........................... 424/81 |
| 5,019,377 | 5/1991 | Torgerson ............................. 424/70 |
| 5,021,477 | 6/1991 | Garbe et al. ........................... 424/70 |
| 5,061,481 | 10/1991 | Suzuki et al. ......................... 424/63 |
| 5,100,657 | 3/1992 | Ansher-Jackson et al. ............ 424/70 |
| 5,100,658 | 3/1992 | Bolich et al. .......................... 424/70 |
| 5,104,642 | 4/1992 | Wells et al. ............................ 424/47 |
| 5,104,646 | * 4/1992 | Bolich et al. ..................... 424/70.11 |
| 5,106,609 | 4/1992 | Bolich et al. .......................... 424/70 |
| 5,120,531 | 6/1992 | Wells et al. ........................... 424/70 |
| 5,120,532 | 6/1992 | Wells et al. ........................... 424/70 |
| 5,132,417 | * 7/1992 | Potthoff-Karl et al. ............... 424/71 |

FOREIGN PATENT DOCUMENTS

| | | |
|---|---|---|
| 0323715 | * 12/1988 | (EP) . |
| 0320218 | * 6/1989 | (EP) . |
| 0 408 311 A2 | 1/1991 | (EP) . |
| 0 412 704 | 2/1991 | (EP) . |
| 0 412 707 | 2/1991 | (EP) . |

OTHER PUBLICATIONS

Hercules Inc. Development Data–15 Publication.
Hercules Inc. Development Data–16 Publication.
Hercules Inc. Development Data–32 Publication.
Hercules Inc. Research Publication dated Nov. 2, 1984, entitled "Update WSP D–340 Performance in Surfactant Systems".

* cited by examiner

Primary Examiner—Thurman K. Page
Assistant Examiner—T. Ware
(74) Attorney, Agent, or Firm—Leonard W. Lewis; William J. Winter

(57) ABSTRACT

Hair styling agents, and aqueous base hair care compositions containing them, wherein the hair styling agent comprises a water-insoluble hair styling polymer with a volatile, water-insoluble diluent. The water-insoluble hair styling polymer consists essentially of hydrophobic monomer units. These compositions are particularly useful for application to the hair in the form of a rinse-off hair care composition comprising the hair styling agent and an aqueous carrier providing a gel-like rheology.

17 Claims, No Drawings

HAIR STYLING AGENTS AND COMPOSITIONS CONTAINING HYDROPHOBIC HAIR STYLING POLYMERS

This is a continuation of application Ser. No. 08/156,655, filed on Nov. 22, 1993 now abandoned which is a con of Ser. No. 07/828,848 Jun. 31, 1992, Abn which is a con of Ser. No. 07/712,026, Jun. 7, 1991 Abn.

TECHNICAL FIELD

The present invention relates to hair care compositions containing a hair styling polymer component and an aqueous carrier. The present invention further relates to rinse-off hair care compositions containing an aqueous carrier and a combination of a hair styling component and a hair conditioning component.

BACKGROUND OF THE INVENTION

In washing, drying and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel. Generally, these benefits are provided by a separate, rinse-off hair conditioning product. By "rinse-off" what is meant is that the product is applied to the hair (typically wet hair) and then rinsed off with water prior to drying the hair (or allowing the hair to air dry).

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style and shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. This approach presents several significant drawbacks to the user. It requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition.

It is desirable to provide hair care compositions which provide hair styling benefits to the user without the hair tending to feel sticky or stiff after application. It is also desirable to provide hair care compositions that can be applied to the hair in a rinse-off hair composition that can provide hair styling benefits without causing the hair to feel sticky or stiff after application. It is further desirable to provide hair care compositions providing such hair styling benefits which can also condition the hair in a single composition.

Hair care compositions which meet these objects have, in fact, been provided. Specifically, rinse-off hair care compositions that can style and/or condition the hair are described in U.S. application Ser. Nos. 07/551,118, 07,551,119, and 07/551,120, all filed Jul. 16, 1990 by Bolich, Norton, and Russell. These patent applications describe hair care compositions having a gel-like rheology based upon hydrophobically modified water soluble polymers and can contain hair styling polymers, including silicone macromer-containing hair styling polymers which both condition and style the hair. These compositions can also contain separate hair conditioning ingredients. The silicone macromer-containing polymers, as well as other rinse-off hair care compositions containing them, are also described in U.S. application Ser. No. 07/505,755, filed Apr. 6, 1990 by Bolich and Torgerson and U.S. Ser. No. 07/505,760, filed Apr. 6, 1990, by Torgerson, Bolich, and Garbe.

The compositions described in these patent applications can provide excellent hair styling and conditioning performance. The silicone macromer-containing polymer which is essential to these compositions, however, unfortunately is complex to manufacture and can be significantly more expensive than hair styling polymers not containing silicone macromer units.

U.S. Pat. No. 4,963,348, Bolich and Torgerson, issued Oct. 16, 1990, discloses hair styling agents and compositions containing the same wherein the hair styling agents disclosed are certain adhesive copolymers in a volatile, water-insoluble diluent. The copolymers that are discussed comprise a mixture of relatively hydrophilic monomers that form high glass transition temperature (Tg) homopolymers and less hydrophilic monomers that form lower Tg homopolymers. Exemplary hydrophilic, high Tg-forming monomers are identified as acrylate and methacrylate amides. It would be desirable to provide hair styling agents which do not require incorporation of the relatively hydrophilic acrylate and methacrylate amide monomers, which can make the polymers hygroscopic and sticky to the touch upon application to the hair.

An object of this invention, therefore, is to provide aqueous-base hair care compositions that can provide hair styling benefits without causing the hair to become excessively sticky or stiff and not requiring the use of either the relatively expensive silicone macromer-containing hair styling polymers or the incorporation of hydrophilic monomers into the hair styling polymer. It is especially desirable to provide such compositions which can be applied to the hair in the form of a rinse-off formulation, and which also can include separate hair conditioning ingredients.

These and other objects as may be apparent can be obtained by the invention described as follows.

All percentages reported herein are by weight of the total composition and all ratios reported herein are weight ratios, unless otherwise specifically indicated.

SUMMARY OF THE INVENTION

It has now been found that water-insoluble hair styling polymers consisting essentially of hydrophobic monomer units can fulfill the above objects when admixed with a water-insoluble diluent and delivered to the hair via an aqueous carrier. Previously, it was believed that it was necessary to incorporate hydrophilic monomer units into the polymer to provide sufficient polymer substantivity and therefore good hair styling performance, when the polymer is delivered via a water-insoluble diluent in an aqueous carrier.

Thus, the present invention relates to hair styling agents, and aqueous base hair care compositions containing them, wherein the hair styling agent comprises a hydrophobic, water-insoluble hair styling polymer with a volatile, water-insoluble diluent. The water-insoluble hair styling polymer hereof consists essentially of hydrophobic monomer units. These compositions are particularly useful for application to the hair in the form of a rinse-off hair care composition comprising the hair styling agent and an aqueous carrier providing a gel or gel-like rheology (hereafter, collectively "gel-like rheology"). The use of the hydrophobic, water-insoluble polymers hereof surprisingly has been found to be able to provide excellent hair styling performance without causing the hair to become excessively sticky or stiff.

More particularly, the present invention relates to hair styling agents comprising:

(a) a water-insoluble hair styling polymer consisting essentially of monomer units derived from polymerizable, hydrophobic monomers, said polymer having a weight average molecular weight of at least about 10,000 and a solubility in water at 25° C. of about 0.1% or less, calculated on a water plus polymer weight basis;

(b) a water-insoluble volatile diluent for said hair styling polymer, said diluent having a boiling point, at atmospheric pressure, of less than about 300° C. and a solubility in water at 25° C. of 0.2% or less, calculated on a water plus diluent weight basis;

wherein the weight ratio of said hair styling polymer to said volatile diluent is from about 1:100 to about 5:1.

The present invention encompasses hair care compositions, especially rinse-off hair care compositions, comprising from about 0.1% to about 50% of a hair styling agent as described immediately above and an aqueous carrier suitable for applying the hair styling agent to the hair. The precise level of the aqueous carrier is not critical so long as it is adequate for delivering the hair styling agent to the hair. Generally, it will constitute from about 50% to about 99.9%, by weight, of the composition. Preferably, the aqueous carrier comprises water in combination with other ingredients which can provide a thick, or viscous, rheology. Particularly preferred are gel-like rheologies. It is also preferred to include in the compositions one or more hair conditioning agents, such conditioning agents typically being used at levels of from about 0.01% to about 10% by weight of the composition.

The present invention also relates to a method for providing style hold to hair, said method comprising applying to hair (preferably wet hair that has been shampooed and rinsed) an effective amount of a hair styling composition, or a hair styling and conditioning composition, of the present invention to provide style hold benefits or, in the case of a hair styling and conditioning composition, an effective amount to provide style hold and hair conditioning benefits. The hair can then be dried and styled directly or subsequent to rinsing. Generally, from about 1 g to about 20 g of the composition are applied.

DETAILED DESCRIPTION OF THE INVENTION

The essential components, as well as various preferred and optional components, of the present invention are described below. The method of use of the present invention is also described below.

Hair Styling Agent

The hair styling agent of the present invention comprises a mixture of a water-insoluble, hydrophobic hair styling polymer and a water-insoluble, volatile diluent.

The hair styling agent generally should have a hair styling polymer to volatile solvent weight ratio of from about 1:100 to about 5:1, preferably from about 1:10 to about 1:1, more preferably from about 1:8 to about 2:3.

A. Hair Styling Polymer

The hydrophobic, water-insoluble hair styling polymers hereof consist essentially of monomer units derived from polymerizable hydrophobic monomers. By "hydrophobic monomer" what is meant is a monomer that, upon polymerization with like monomers, forms a water-insoluble homopolymer.

By "water-insoluble" polymer what is meant is that the polymer has a solubility in water at 25° C. of about 0.1% or less, calculated on a water plus polymer weight basis. "Solubility" for purposes hereof corresponds to the maximum concentration of polymer that can dissolve in water to form a solution that is substantially clear to the naked eye, as is well understood to those skilled in the art.

The hair styling polymer preferably has a glass transition temperature, Tg, (i.e., the temperature at which the polymer changes from a brittle vitreous state to a plastic state) of at least about −20° C., preferably between about 0° C. and about 80° C., and most preferably between about 20° C. and about 60° C. Tg can be determined by differential scanning calorimetry.

The hair styling polymers consist essentially of the monomer units derived from the hydrophobic monomers. By "consist essentially of" is meant that the polymers can contain other monomer units which are not hydrophobic, however the polymer must remain water-insoluble as defined above. Additionally, the polymers hereof do not contain silicone macromer units and do not contain substantial levels (no more than about 5% by weight of the polymer, preferably no more than about 1%, more preferably zero or essentially zero percent) of amide-containing monomer units.

The hair styling polymers of the present invention will have a weight average molecular weight of at least about 10,000. The molecular weight will generally be less than about 5,000,000, although higher molecular weights are not intended to be excluded. Preferably, the weight average molecular weight will be from about 30,000 to about 5,000,000, more preferably at least about 50,000, even more preferably at least about 75,000. The weight average molecular weight is preferably less than about 200,000, more preferably less than about 150,000. Weight average molecular weight, for purposes hereof, can be measured by methods known in the art suitable for determining molecular weight of the sample to be analyzed, for example size exclusion chromatography utilizing column pore sizes of $10^3$, $10^5$, and $10^6$ angstroms, or other equivalent method.

Suitable hydrophobic monomers include acrylic or methacrylic acid esters of $C_1$–$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and methoxy ethyl methacrylate. The polymers hereof can be homopolymers of such hydrophobic monomers or can be co-, ter-, etc. polymers of hydrophobic monomers.

Preferred monomers include n-butyl methacrylate, isobutyl methacrylate, 2-ethylhexyl methacrylate, methyl methacrylate, t-butylacrylate, t-butylmethyacrylate, and mixtures thereof. Especially preferred are homopolymers of t-butylacrylate.

The polymers hereof can be made by conventional polymreization techniques well known in the art including, for example, free radical polymerization.

B. Volatile Diluent

The hair styling agent hereof additionally comprises a water-insoluble, volatile diluent in which the hair styling polymer is admixed. Thus, the hair styling polymer should be soluble or dispersible in the diluent.

The volatile diluent has a boiling point, at atmospheric pressure, of less than about 300° C., preferably from about 100° C. to about 300° C., and a solubility in water at 25° C. of 0.2% or less, preferably about 0.1% or less, on a water plus volatile diluent weight basis.

The volatile diluents useful in the present compositions include hydrocarbons, esters, ethers, alkyl alcohols, silicon derivatives, and mixtures thereof. Preferred are the ester, ether, alkyl alcohol, and hydrocarbon fluids.

The hydrocarbons may be either straight or branched chain and may contain from about 10 to about 16, preferably from about 12 to about 16 carbon atoms. Examples of suitable hydrocarbons are decane, dodecane, decene, tridecane and mixtures thereof. Also useful are the terpenes such as orange and lemon terpenes.

Useful alkyl alcohols can be saturated or unsaturated and branched or straight chain. Suitable alkyl alcohols include, for example, linalool and decyl alcohol.

The volatile silicon derivatives useful in the compositions of the present invention include cyclic and linear polydialkyl-siloxanes, and silanes.

The number of silicon atoms in the cyclic silicones is preferably from about 3 to about 7, more preferably about 3 to about 5. The general formula for such cyclic silicones is:

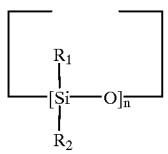

wherein $R_1$ and $R_2$ are independently selected from $C_1$ to $C_8$ alkyl, aryl or alkylaryl and wherein n=3–7.

The linear polyorgano siloxanes have from about 2 to 7 silicon atoms and have the general formula:

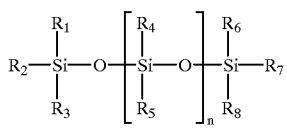

wherein $R_1$, $R_2$, $R_3$, $R_4$, $R_5$, $R_6$, $R_7$, and $R_8$ can independently be saturated or unsaturated $C_1$–$C_8$ alkyl, aryl, alkyl aryl, hydroxyalkyl, amino alkyl or alkyl siloxy, and n=1–7.

Silane compounds have the general formula:

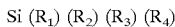

wherein $R_1$, $R_2$, $R_3$, and $R_4$ can independently be selected from $C_1$–$C_8$ alkyl, aryl, alkyl aryl, hydroxy alkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes.

A description of volatile silicones is found in Todd and Byers, "Volatile Silicone Fluids for Cosmetics", *Cosmetics and Toiletries,* Vol. 91, January, 1976, pp 27–32, and also in *Silicon Compounds,* pages 253–295, distributed by Petrarch Chemicals, both of which are incorporated herein by reference.

Useful esters include, for example, methyl alkanoates such as the $C_8$–$C_{12}$ alkanoates (e.g., methyl decanoate), di($C_2$–$C_3$)alkyl adipates (e.g., diethyl adipate, diisopropyl adipate), $C_8$–$C_{10}$ alkyl acetates (e.g., octyl acetate), and benzoates (e.g., butyl benzoate).

Useful ethers include di($C_5$–$C_7$) alkyl ethers, especially the di($C_5$–$C_6$) alkyl ethers such as dipentyl ether and dihexyl ether.

Especially preferred are mixtures of volatile silicones with ester, ether and/or hydrocarbon diluents, particularly mixtures of silicones and esters (e.g., diisopropyl adipate). The weight ratio of silicone to the other diluent(s) will generally be about 1:10 to about 10:1.

Optionally, water-insoluble, non-volatile diluents can be included in the hair styling agent. Non-volatile diluents may be used, for example, to help to dissolve the hair styling polymer. Preferred non-volatile diluents include liquid alcohols and liquid fatty acids such as isocetyl alcohol, oleyl alcohol, oleic acid, and isostearic acid.

In order to form the hair styling agent, the hair styling polymer is admixed with the volatile diluent preferably in a weight ratio of from about 1:100 to about 5:1, more preferably from about 1:10 to about 1:1, and most preferably from about 1:8 to about 2:3. The hair styling agents should have an average particle diameter of from about 0.5 to about 100 microns, preferably from about 1 micron to about 25 microns. Particle size can be measured according to methods known in the art, including, for example optical microscopy.

Hair Care Compositions

The aqueous base hair care compositions hereof will typically comprise from about 0.1% to about 50%, by weight, of the hair styling agent hereof, preferably from about 0.2% to about 30%, more preferably from about 0.5% to about 15%, and an aqueous carrier suitable for applying the hair styling agent to the hair. In general, the hair care compositions will have a hair styling polymer to volatile diluent weight ratio as previously described. The aqueous carrier will typically be present in the composition at levels of from about 50% to about 99.9%, preferably from about 70% to about 99%, more preferably from about 85% to about 99%.

The hair care compositions are of at least two phases: at least one phase being the hair styling agent and at least one phase being the aqueous carrier. The term "aqueous carrier suitable for applying the hair styling agent to hair" as used herein, means water or one or more compatible water-based vehicles which are suitable for administration to the hair of a human or lower animal. The term "compatible", as used herein, means that the components of the carrier are capable of being commingled with the hair styling agent of the present invention, and with each other, in a manner such that there is no interaction which would substantially inhibit the ability of the hair styling polymers to provide temporary set hold to hair under ordinary use situations. These carriers must, of course, be of sufficiently low toxicity to render them suitable for administration to the hair of the human or lower animal to which they are being applied.

Other phases which do not form a part of the hair styling agent or the aqueous carrier may also be present. Types of these phases are exemplified below. For purposes herein, ingredients which are soluble in water or interact in water with other ingredients to form a gel or create a gel-like rheology or which otherwise reduce or inhibit separation of (i.e., stabilize) water-insoluble ingredients in the composition are part of the aqueous carrier, including multiple function components which meet the above criteria.

Carriers suitable for applying the styling agents such as shampoos and cream rinse conditioner to hair are well known in the art; their selection can be made without difficulty by a person skilled in the art.

The aqueous carriers used herein include water and may also include other fluids in addition to water and other carrier components used in hair care compositions. The styling agent components should be insoluble in the the carrier fluid system, whether the carrier fluid is just water or a mixture of water and other fluid. Suitable carrier fluids for use in the present invention, in addition to water, include lower alcohols ($C_1$–$C_4$ alcohols, preferably $C_2$–$C_4$ alcohols such as ethanol and isopropanol) and mixtures of lower alcohols. Preferred solvents include water, ethanol, and mixtures thereof. When water-lower alcohol mixtures are used, the water:lower alcohol weight ratio is typically in the range of from about 20:1 to about 1:2; most preferably, water is the primary solvent in the carrier and alcohol solvent levels are below about 20%, preferably essentially zero, by weight of the composition.

The carrier may include thickening materials to increase viscosity of the composition. Preferred materials that can be used are gel vehicle materials. In essence, these materials form a gel network, in combination with the water or other carrier fluid. The gel vehicle comprises two essential components: a lipid or lipid-like vehicle material and a cationic surfactant vehicle material. A variety of suitable cationic surfactant materials are described in detail below. The cationic surfactant can also provide separate hair conditioning benefits. Gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000—Cetostearyl Alcohol, I. Self Bodying Action", 38 *J. of Colloid and Interface Science* 616–625 (1972).

The gel vehicles may incorporate one or more lipid material hereafter referred to as "lipid vehicle materials", which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from about 12 to about 22, preferably from about 16 to about 18, carbon atoms in length. Fatty alcohols and fatty esters are preferred; fatty alcohols are particularly preferred.

Lipid vehicle materials among those useful herein are disclosed in *Bailey's Industrial Oil and Fat Products,* (3rd edition, D. Swern, ed., 1979), incorporated by reference herein. Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465, Kaufman, et al., issued Sep. 12, 1976 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl stearyl alcohol.

If gel vehicle materials are included in the compositions of the present invention, the lipid vehicle material is generally present at from about 0.1% to about 10.0% of the composition, and the cationic surfactant vehicle material is generally present at from about 0.5% to about 5.0% of the composition.

Water-soluble polymeric thickeners can also be used to thicken conditioner compositions and stabilize insoluble components. These include natural polysaccharides such as guar gum, xanthan gum and locust bean gum.

Nonionic water-soluble cellulose ethers are preferred polymers that can be employed in hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Preferred carrier vehicles for use in the compositions of the present invention include hydrophobically-modified nonionic water soluble polymer (preferably the nonionic water-soluble polymer is hydroxyethyl cellulose), in combination with certain surfactants and solvents, as described in detail in the following patent applications, each of which is incorporated herein by reference: U.S. Ser. Nos. 07/551,118, 07/551,119, and 07/551,120, all filed Jul. 16, 1990, by Bolich, Norton, and Russell. These systems provide a gel-like rheology without necessarily being gels in the technical sense. By "hydrophobically modified nonionic water-soluble polymer" is meant a nonionic water-soluble polymer which has been modified by the substitution with a sufficient amount of hydrophobic groups to make the polymer less soluble in water. By "water-soluble" what is meant is the polymer or salt, thereof, constituting the polymer backbone of the thickener should be sufficiently soluble such that it forms a substantially clear solution when dissolved in water at a level of 1%, by weight of the solution, at 25° C. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

A number of references teach the use of nonionic cellulose ethers and water-soluble gums for thickening hair care compositions. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum, each incorporated herein by reference.

Certain cellulose ethers have been disclosed in U.S. Pat. No. 4,228,277, Landoll, issued Oct. 14, 1980, incorporated herein by reference, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

Any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

One commercially available material which meets these requirements is NATROSOL PLUS Grade 430, hydrophobically modified hydroxyethylcellulose available from Aqualon Company, Wilmington, Del. This material has a $C_{16}$ alkyl substitution of about 0.5% to about 0.9% by weight. The hydroxyethyl molar substitution for this material is from about 2.8 to about 3.2. The average molecular weight for the water-soluble cellulose prior to modification is approximately 300,000.

The most preferred material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3. The average molecular weight for the water-soluble cellulose prior to modification is approximately 700,000.

These modified cellulose ethers have been disclosed for use in a variety of composition types. Landoll ('277) teaches the use of these materials in shampoo formulations. Hercules trade literature teaches the use of these materials in shampoos. U.S. Pat. No. 4,683,004, Goddard, issued Jul. 28, 1987, discloses the use of these materials in mousse compositions for the hair.

These materials can be used with certain secondary thickening materials to provide a gel-like rheology.

One category of secondary thickening material is a water-soluble polymeric material, having a molecular weight greater than about 20,000. By "water-soluble polymeric thickening material" is meant that the material will form substantially a clear solution in water at a 1% concentration at 25° C. and the material will increase the viscosity of the water. Examples of water-soluble polymers which are desirably used as the additional thickening component in the present vehicle systems, include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethylcellulose, plant exudates such as acacia, ghatti, and tragacanth, seaweed extracts such as sodium alginate, propylene glycol alginate, sodium carrageenan, and Ucare JR-polymer (a cationic modified hydroxyethyl cellulose available from Union Carbide). Preferred as the additional thickener for the present vehicle systems are natural polysaccharide materials. Examples of such materials are guar gum, locust bean gum, and xanthan gum. Also preferred as the additional thickener in the present compositions is hydroxyethylcellulose having a molecular weight of about 700,000.

When such systems are used to thicken the present compositions, from about 0.3% to about 5.0%, preferably from about 0.4% to about 3.0%, of the hydrophobically modified hydroxyethyl cellulose is utilized with from about 0.3% to about 5.0%, preferably from about 0.4% to about 3.0%, of the water-soluble polymeric material.

An alternative secondary thickening material for the hydrophobically modified hydroxyethyl cellulose is a water-soluble surfactant having a molecular weight of less than about 20,000. By "water-soluble surfactant" is meant surfactant materials which form substantially clear, isotropic solutions when dissolved in water at 0.2 weight percent at 25° C.

Essentially any water-soluble surfactant material which meets these requirements will work in the present invention. However, the following materials have been found to be particularly preferred: cetyl betaine, ammonium lauryl sulfate, ammonium laureth sulfate, cetyl trimethyl ammonium chloride, and mixtures thereof.

When such systems are used to thicken the present compositions, from about 0.1% to about 10.0%, preferably from about 0.2% to about 5.0%, of the hydrophobically-modified hydroxyethyl cellulose is generally utilized with from about 0.02% to about 0.30%, preferably from about 0.05% to about 0.30%, most preferably from about 0.05% to about 0.20%, of the water-soluble surfactant. The water-soluble surfactant level is kept low because higher levels of water-soluble surfactants interfere with the hydrophobically-modified hydroxyethyl cellulose thickener and produce compositions with much less desirable rheologies.

The preferred secondary thickening material for the hydrophobically-modified hydroxyethyl cellulose is a water-insoluble surfactant having a molecular weight of less than about 20,000. By "water-insoluble surfactant" is meant surfactant materials which do not form substantially clear isotropic solutions when dissolved in water at greater than 0.2 weight percent at 25° C.

Essentially any water-insoluble surfactant material which meets these requirements will work in the present invention, however, water-insoluble cationic surfactant materials are preferred. The following nonexclusive materials are suitable: stearamide diethanolamine (stearamide DEA), cocoamide methanolamine (cocoamide MEA), dimethyl stearamine oxide, glyceryl mono-oleate, sucrose stearate, PEG-2 stearamine, Ceteth-2, a polyethylene glycol ether of cetyl alcohol of the formula $CH_3-(CH_2)_{14}-CH_2-(OCH_2CH_2)n-OH$, where n has an average value of 2 (commercially available under the trade name Brij 56 from ICI Americas), glycerol stearate citrate, dihydrogenated tallow dimethyl ammonium chloride, Poloxamer 181, a polyoxyethylene, polyoxypropylene block polymer of the formula

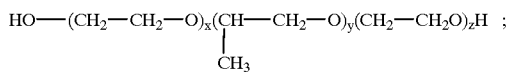

wherein on average x=3, y=30 and z=3 (commercially available from BASF Wyandotte under the trade name Pluronic L-61), hydrogenated tallow dimethyl betaine, and hydrogenated tallow amide DEA.

When such systems are used to thicken the present compositions, from about 0.1% to about 10.0%, preferably from about 0.2% to about 5.0%, of the hydrophobically-modified hydroxyethyl cellulose is generally utilized with from about 0.02% to about 10.0%, preferably from about 0.05% to about 3.0%, most preferably from about 0.05% to about 2.0%, of the water-insoluble surfactant.

Cationic surfactants useful in carrier systems of the compositions of the present invention, including the gel vehicle systems as well as hydrophobically modified cellulose vehicle systems, contain amino or quaternary ammonium hydrophilic moieties which are positively charged when dissolved in the aqueous composition of the present invention. Cationic surfactants among those useful herein are disclosed in the following documents, all incorporated by reference herein: *McCutcheon's, Emulsifiers & Detergents,* (1989, published by the M.C. Publishing Company) Schwartz, et al., *Surface Active Agents, Their Chemistry and Technology,* New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Quaternary ammonium salts include dialkyldimethyl-ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride are exemplary quaternary ammonium salts useful herein.

Particularly useful cationic surfactants for use as thickeners and conditioners in carrier vehicles containing the hydrophobically modified water soluble polymers described above are selected from quaternary ammonium surfactants having the formula, in salt form:

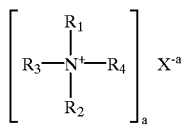

(I)

wherein X is a salt-forming anion, a is the ionic charge of X, the quaternary ammonium radicals $R_1$, $R_2$, $R_3$, and $R_4$ independently are $C_1$–$C_{22}$ alkyl, $C_{14}$–$C_{22}$ alkyl amido $C_2$–$C_6$ alkylene, or benzyl, and from two to three of said quaternary ammonium radicals, preferably two, are $C_{14}$–$C_{22}$ alkyls or $C_{14}$–$C_{22}$ alkyl amido $C_2$–$C_6$ alkylene (preferably $C_2$–$C_3$ alkylene), preferably $C_{16}$–$C_{22}$ alkyl, more preferably $C_{16}$–$C_{18}$ alkyl, or mixtures thereof, no more than two of said radicals are either $C_{14}$–$C_{22}$ alkyl amido $C_2$–$C_6$ alkylene or a combination of $C_{14}$–$C_{22}$ alkyl and $C_{14}$–$C_{22}$ alkyl amido $C_2$–$C_6$ alkylene, from one to three of said quaternary ammonium radicals, preferably two or three, are $C_1$–$C_6$ alkyls, preferably $C_1$–$C_3$ alkyl, more preferably methyl, and no more than one of said radicals is benzyl; or

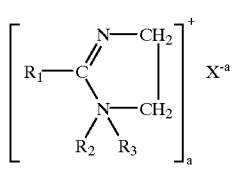

(II)

wherein X and a are as defined above, the radicals $R_1$, $R_2$, and $R_3$ independently are $C_1$–$C_{22}$ alkyl or benzyl, preferably $C_1$–$C_{22}$ alkyl, and one or two of said radicals are $C_{14}$–$C_{22}$ alkyls, preferably $C_{16}$–$C_{22}$ alkyl, or $C_{14}$–$C_{22}$ alkyl amido $C_2$–$C_6$ alkylene (preferably $C_2$–$C_3$ alkylene), or a mixture thereof, one or two of said radicals are $C_1$–$C_6$ alkyl, preferably $C_1$–$C_3$ alkyl, more preferably methyl, zero or one of said radicals is benzyl, wherein the quaternary ammonium surfactant component of the above description has a sufficient level unsaturation in the $C_{14}$–$C_{22}$ alkyl or $C_{14}$–$C_{22}$ alkyl amido $C_2$–$C_6$ alkylene radicals, or mixtures thereof, such that average iodine value of said component is at least about 15; or a mixture of Formula I and II surfactants.

Another specific category of cationic quaternary ammonium surfactants that can be advantageously incorporated into the present compositions, particularly in combination with the above-described essential unsaturated quaternary ammonium surfactants, are water-insoluble materials having the formula, in salt form,

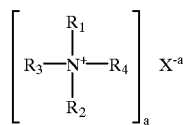 (III)

wherein X is a salt-forming anion as previously described, a is the charge of the anion X, the radicals $R_1$, $R_2$, R3, and $R_4$ independently are $C_1$–$C_6$ alkyl, $C_{20}$–$C_{22}$ alkyl, or benzyl wherein one of said radicals is $C_{20}$–$C_{22}$ alkyl, preferably $C_{22}$, from two to three of said radicals are $C_1$–$C_6$ alkyl, preferably $C_1$–$C_3$, more preferably methyl, and zero or one of said radicals is benzyl.

The long chain alkyl (i.e. the $C_{20}$–$C_{22}$ alkyl) can be either saturated or unsaturated.

An exemplary quaternary ammonium surfactant of Formula III is dimethyl behenyl benzyl ammonium salt (alternately referred to as behenalkonium salt), available from Witco Chemical Corp. (Memphis, Tenn., USA) as a chloride salt under the trade name Kemamine® BQ-280$_2$C. Another Formula III material is dimethyl arachidyl benzyl ammonium salt.

The quaternary ammonium surfactant of Formula III is generally used at a level of from about 0.02% to about 10.0%, preferably from about 0.05% to about 3.0%, more preferably from about 0.05% to about 2.0%, by weight, of the composition.

Preferred combinations are compositions containing the surfactant of Formula III, especially in saturated form, in combination with the surfactants of Formulas I or II, or a mixture thereof, wherein the Formula I and II component comprises $C_{14}$–$C_{18}$ unsaturated alkyls, preferably at a weight ratio of (Formulas I and II):(Formula III) of about 1:1 to about 4:1.

Another combination of cationic surfactants that can be used comprises a mixture of di(unsaturated) $C_{16}$–$C_{18}$ alkyl (preferably tallow) dimethyl ammonium salt (e.g. the chloride salt as commercially available from Sherex Chemicals under the tradename ADOGEN 470)) and dimethyl (saturated or unsaturated behenyl and/or arachidyl, preferably saturated) benzyl ammonium salt (e.g. the chloride salt, at a weight ratio of about 1:1 at about 4:1, more preferably about 1:1 to about 3:1.

Salts of primary, secondary and tertiary fatty amines are also suitable for use herein. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tri(decyl) amine, ethyl stearylamine, ethoxylated (2 moles E.O.) stearylamine, dihydroxyethyl stearylamine, and arachidyl-behenylamine. Suitable amine salts include the halogen, acetate, phosphate, nitrate, citrate, lactate and alkyl sulfate salts. Such salts include stearylamine hydrochloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

The compositions of the present invention may also contain other materials which provide additional rheological benefits to the cosmetic compositions formulated therewith, e.g., chelating agents. In general, such materials include monodentate and multidentate agents. Specific examples of useful chelating agents include ethylenediaminetetraacetic acid (EDTA), and salts thereof, nitrilotriacetic acid (NTA) and salts thereof, hydroxyethyl ethylene diamine triacetic acid (HEEDTA) and salts thereof, diethylene triamine pentaacetic acid (DTPA) and salts thereof, diethanolglycine (DEG) and salts thereof, ethanol diglycine (EDG) and salts thereof, citric acid and salts thereof, phosphoric acid and salts. The most preferred of these is EDTA. The chelating agents tend to make the compositions smoother and less gelatinous in consistency.

If a chelating agent is present as a rheological aid in the compositions of the present invention, it is generally used at a level of from about 0.05% to about 1.0%, preferably from about 0.05% to about 0.3%, of the composition.

Optional Ingredients

Other ingredients useful in hair care styling and conditioning compositions can also be included in the compositions hereof, and can be routinely chosen by one skilled in the hair care product art.

Particularly preferred ingredients are hair conditioning agents, such as the cationic surfactants previously described, and silicone conditioning agents.

Silicone conditioning agents include both volatile and non-volatile silicone fluids. Volatile silicones useful herein have been previously described.

Nonvolatile silicone fluids can also useful as active hair care components in the compositions of the present invention. "Nonvolatile" means that the silicone material has essentially no vapor pressure at one atmosphere, at 25° C. Nonvolatile silicones will generally have a boiling point in excess of about 250° C. and a viscosity in excess of about 10 centipoise at 25° C. Those skilled in the art will recognize that slight vapor pressures may sometimes be measured for some fluids which are not of practical significance in silicone conditioner product formulation. These materials are meant to be included herein as nonvolatile fluids. Examples of such materials include polydimethylsiloxanes (fluids and gums), aminosilicones and phenylsilicones.

Suitable alkyl and aryl groups for polyalkyl and polyaryl siloxanes include methyl, methoxy, ethoxy, propoxy, aryloxy, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone materials include cationic materials of the formula:

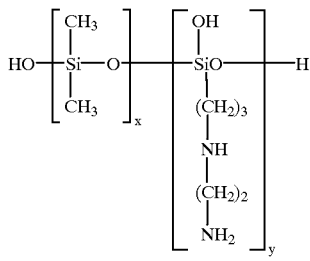

in which x and y are integers which depend on the molecular weight, the average molecular weight being approximately between 5,000 and 10,000. This polymer is also known as "amodimethicone".

Silicone cationic polymers are described in European Patent Application EP 95,238. A preferred polymer corresponding to this formula is the polymer known as "trimethylsilylamodimethicone" of formula:

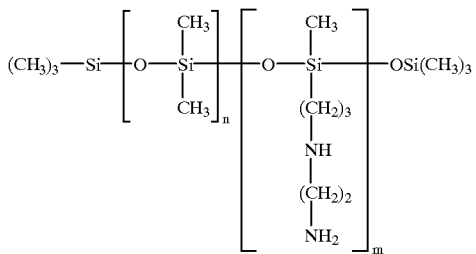

Compositions of the present invention typically comprise no more than about 1.0% of a trimethylsilyl amodimethicone silicone conditioning material.

Other silicone cationic polymers which can be used in the present compositions correspond to the formula:

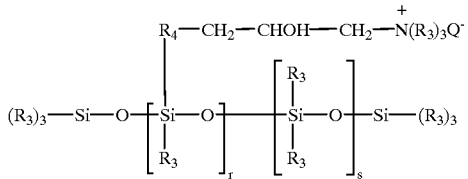

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_8$, alkyleneoxy radical;

Q– is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017, incorporated herein by reference.

A polymer of this class is sold by UNION CARBIDE under the name "UCAR SILICONE ALE 56".

Silicone conditioning agents are optionally used in the present compositions, generally at levels of from about 0.1% to about 18%, preferably from about 0.5% to about 15%.

Preferred silicone conditioning agents for use in the present compositions comprise combinations of volatile silicone fluids having viscosities of less than about 10 centipoise, and from about 0.015% to about 9.0%, preferably from about 0.5% to about 2.0%, of silicone gums having viscosities of greater than about 1,000,000 centipoise, at ratios of volatile fluid to gum of from about 90:10 to about 10:90, preferably from about 85:15 to about 50:50.

Alternative preferable nonvolatile silicone materials for use in the present invention comprise non-volatile silicone fluids having viscosities of less that about 100,000 cP (centipoise), and from about 0.015% to about 9.0%, preferably from about 0.5% to about 2.0%, of silicone gums having viscosities greater than about 1,000,000 cP, especially polydimethylsiloxane gums and polyphenylmethylsiloxane gums, at ratios of non-volatile fluid to gum of from about 70:30 to about 30:70, preferably from about 60:40 to about 40:60.

The efficacy of nonvolatile silicone hair conditioning agents can be enhanced through the use of silicone resins which are mixable with the silicone hair conditioning agent. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone resins will generally have at least about 1.1 oxygen atoms per silicon atom. Preferably, the ratio of oxygen:silicon atoms is at least about 1.2:1.0. Typical silanes used in the manufacture of silicone resins are monomethyl-, dimethyl-, monophenyl-, diphenyl-, methylphenyl-, monovinyl-, and methylvinylchlorosilanes, and tetrachlorosilane. Preferred resins are the methyl substituted silicone resins, such as those offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such non-hardened form rather than as a hardened resin, as will be readily apparent to those skilled in the art.

The weight ratio of the nonvolatile silicone fluid conditioning component to the silicone resin component is preferably from about 4:1 to about 400:1. More preferably such ratio is from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum, as described above.

Hydrolyzed animal protein hair conditioning agents may also be included in the present compositions. Such materials are typically used at levels of from about 0.1% to about 1.5% of the composition. An example of a commercially available material is sold under the tradename Crotein Q® from Croda, Inc.

Combinations of the aforementioned conditioning agents may also be used in the present compositions.

A distributing aid may be included in the composition. Such a material helps to distribute the composition onto the hair avoiding localized deposition of the active component onto the hair or skin.

Examples of water soluble polymer materials which meet these requirements and hence, can act as distributing aids in the present compositions, include: xanthan gum; Dextran purified crude Grade 2P available from D&O chemicals; carboxymethyl celluloses; for example, CMC's 4H1F, 4M6F, 7HF, 7M8SF, 7LF, 9H4F, 9M8, 12M8P, 16M31, (all available from Aqualon); plant exudates such as acacia, ghatti and tragacanth; seaweed extracts such as sodium alginate, propylene glycol alginate, and sodium carrageenan; high molecular weight hydroxyethyl celluloses such as Natrosol 250H and Natrosol 250HHR (available from Aqualon); and pectin.

If a distributing aid is present in the compositions of the present invention, it should be present at a level of from about 0.02% to about 2.5%, preferably from about 0.05% to about 1.0%, of the composition. If the distributing aid is bifunctional, i.e., acting as part of the carrier and the distributing aid, it may be present at higher levels.

The compositions can also contain a nonvolatile plasticizer as an optional component of the hair styling agent. Such plasticizers are typically used in the compositions at a plasticizer: hair styling polymer weight ratio of about 1:20 to about 1:1, preferably from about 1:15 to about 1:2. As used herein, "non-volatile" in regard to plasticizers means that the plasticizer exhibits essentially no vapor pressure at atmospheric pressure and 25° C. It is also highly preferred that the plasticizer not be odoriferous to the human nose, as any substantial plasticizer odor would affect perfumery of the product. The plasticizer should also be compatible with the hair styling agent.

Plasticizers are well known in the art and are generally described in *Kirk-Othmer Encyclopedia of Chemical Technology*, second edition, Volume 15, pp. 720–789 (John Wiley & Sons, Inc. New York, 1968) under the topic heading "Plasticizers", and by J. Kern Sears and Joseph R. Darby in the text *The Technology of Plasticizers* (John Wiley & Sons, Inc., New York, 1982), both incorporated herein by reference. See especially in the Appendix of Sears/Darby Table A.9 at pages 983–1063 where a wide variety of plasticizers are disclosed.

Plasticizers include both cyclic and acyclic nonvolatile materials. Suitable categories of nonvolatile plasticizers include adipates, phthalates, isophthalates, azelates, stearates, citrates, trimellitates, silicone copolyols iso $C_{14}$–$C_{22}$ alcohols, methyl alkyl silicones, carbonates, sebacates, isobutgrates, oleates, phosphates, myristates, ricinoleates, pelargonates, valerates, oleates, camphor, and castor oil, and silicone copolyols.

Examples of adipate plasticizers include adipic acid derivatives such as diisobutyl adipate, bis(2-ethylhexyl) adipate, diisodecyl adipate, bis(2-butoxyethyl) adipate, and di-n-hexyl adipate.

Examples of phthalate plasticizers include phthalic acid derivatives such as dibutyl phthalate, butyl octyl phthalate, di-n-octyl phthalate, diisooctyl phthalate, bis(2-ethylhexyl) phthalate, n-octyl n-decyl phthalate, di-n-hexyl phthalate, isooctyl isodecyl phthalate, diisodecyl phthalate, ditridecyl phthalate, butyl cyclohexyl phthalate, diisoctyl benzyl phthalate, butyl benzyl phthalate, dicyclohexyl phthalate, diphenyl phthalate, isodecyl benzyl phthalate, and bis(2-butoxyethyl) phthalate.

Isophthalate plasticizers include bis(2-ethylhexyl) isophthalate, and diisooctyl benzyl phthalate.

Examples of azelate plasticizers include azelaic acid derivatives such as di(2-ethylhexyl) azelate, and bis(2-ethylhexyl) azelate.

Examples of stearate plasticizers include stearic acid derivatives such as n-butyl stearate, butyl acetoxystearate, and butoxyethyl stearate.

Examples of citrate plasticizers include citric acid derivatives such as acetyl tri-n-butyl citrate, tri-n-butyl citrate, and acetal tri-2-ethyl hexyl citrate.

Examples of trimellitate plasticizers include tri-(2-ethylhexyl) trimellitate, and triisooctyl trimellitate.

Other examples of plasticizers include dibutyl carbonate, butyl oleate, n-butyl, butyrate, isobutyl butyrate, isopropyl butyrate, dibutyl carbonate, ethyl palmitate, isooctyl palmitate, methyl ricinoleate, butyl ricinoleate, diisooctyl sebacate, triisobutyl phosphate, isodecy pelargonate, ethyl valerate, isocetyl alcohol, octododecanol, isopropyl myristate, isostearyl alcohol and methyl alkyl silicones having $C_2$–$C_{20}$ alkyl and from 1 to about 500 siloxane monomer units.

Silicone copolyols that can be used as plasticizers include polyalkylene oxide-modified polydimethylsiloxane. Polydimethylsiloxane copolyols are also disclosed in the following patent documents, all incorporated by reference herein: U.S. Pat. No. 4,122,029, Gee, et al., issued Oct. 24, 1978; U.S. Pat. No. 4,265,878, Keil, issued May 5, 1981; and U.S. Pat. No. 4,421,769, Dixon, et al., issued Dec. 20, 1983. Such dimethicone copolyol materials are also disclosed, in hair compositions, in British Patent Application 2,066,659, Abe, published Jul. 15, 1981 (incorporated by reference herein) and Canadian Patent 727,588, Kuehns, issued Feb. 8, 1966 (incorporated by reference herein). Commerically available dimethicone polydimethylsiloxane copolyols which can be used herein, include Silwet Surface Active Copolymers (manufactured by the Union Carbide Corporation); and Dow Corning Silicone Surfactants (manufactured by the Dow Corning Corporation).

Other optional ingredients include pearlescent aids, such as ethylene glycol distearate (which may also provide a thickening or suspending benefit, and thereby also be included as a component of the carrier system); preservatives, such as benzyl alcohol, methyl paraben, propyl paraben and imidazolidinyl urea; sodium chloride; sodium sulfate; polyvinyl alcohol; ethyl alcohol; pH adjusting agents, such as citric acid, sodium citrate, succinic acid, phosphoric acid, sodium hydroxide, and sodium carbonate; coloring agents, such as any of the FD&C or D&C dyes; hair oxidizing (bleaching) agents, such as hydrogen peroxide, perborate and persulfate salts; hair reducing agents, such as the thioglycolates; anti-dandruff active ingredients; perfumes; sequestering agents, such as disodium ethylenediamine tetra-acetate; glycerin and propylene glycol. Such optional ingredients generally are used individually at levels of from about 0.01% to about 10.0%, preferably from about 0.05% to about 5.0%, of the composition.

The following examples illustrate the present invention. It will be appreciated that other modifications of the present invention within the skill of those in the cosmetic composition formulation art can be undertaken without departing from the spirit and scope of this invention.

EXAMPLE I

A Styling Rinse Composition is made by combining the following components.

| Component | Weight % |
|---|---|
| Styling Agent | |
| Poly(n-butyl)methacrylate[3] | 2.00 |
| Butyl benzoate | 6.00 |
| Main Mix | |
| Veegum[1] | 1.40 |
| Xanthan gum | 1.40 |
| Cyclomethicone (tetramer) | 0.90 |
| Silicone gum[2] | 0.30 |
| Decyl alcohol | 0.80 |
| Kathon CG | 0.03 |
| DRO $H_2O$ | q.s. |

[1]Magnesium aluminum silicate offered by R. T. Vanderbilt Co.
[2]G.E.S.E. 76
[3]Weight average molecular weight from about 30,000 to about 200,000.

The styling agent is preblended in a conventional manner known to one skilled in the art by conventional methods including low shear operations such as a propeller stirrer as well as high shear methods such as colloidal milling.

EXAMPLE II

A Styling/Conditioning Hair Rinse Composition is made by combining the following components.

| Component | Weight % |
|---|---|
| Styling Agent | |
| Poly(t-butyl) acrylate[5] | 3.00 |
| Methyl decanoate | 9.00 |
| Premix | |
| Silicone gum[4] | 0.10 |
| Cyclomethicone (pentamer) | 0.50 |
| Main Mix | |
| Distearyl dimethyl ammonium chloride | 0.85 |
| Natrosol 250M[1] | 0.50 |
| Dow Corning 190[2] | 0.10 |
| Cetyl alcohol | 1.00 |
| Stearyl alcohol | 1.00 |
| Cetareth-20 | 0.35 |
| Lexamine S-13[3] | 0.50 |
| Perfume | 0.10 |
| Kathon CG | 0.03 |
| DRO $H_2O$ | q.s. |

[1]Hydroxyethylcellulose offered by Hercules, Inc.
[2]A silicone copolyol offered by Dow Corning Corp.
[3]A fatty amine offered by Inolex Chemical Division of American Can Company
[4]G.E.S.E. 76
[5]Weight average molecular weight of from about 75,000 to about 150,000.

The styling agent and premix are blended separately and combined with the main mix as described in Example I.

EXAMPLE III

A Conditioner Composition is made by combining the following components according to conventional mixing technology as described in Example I.

| Component | Weight % |
|---|---|
| Styling Agent | |
| Poly(isobutyl) methacrylate[1] | 0.40 |
| Orange terpenes | 2.00 |
| Main Mix | |
| Stearalkonium chloride | 1.00 |
| Cetrimonium chloride | 0.50 |
| Cetyl alcohol | 1.20 |
| Stearyl alcohol | 0.50 |
| Ceteth-2 | 1.00 |
| Glyceryl monostearate | 0.50 |
| Sodium chloride | 0.05 |
| Kathon CG | 0.03 |
| DRO $H_2O$ | q.s. |

[1]Weight average molecular weight of from about 75,000 to about 150,000.

EXAMPLE IV

A Conditioner Composition is made by combining the following components according to conventional mixing technology as described in Example II.

| Component | Weight % |
|---|---|
| Styling Agent | |
| Poly(t-butyl) acrylate[4] | 3.00 |
| $D_4$ cyclomethicone | 6.75 |
| Linalool | 2.25 |
| Premix | |
| $D_5$ cyclomethicone | 1.70 |
| Silicone gum[1] | 0.30 |
| Main Mix | |
| Dow Corning 190 silicone surfactant | 0.50 |
| Cetyl alcohol | 0.99 |
| Stearyl alcohol | 0.66 |
| Lexamine S-13[2] | 0.50 |
| Ceteareth-20 | 0.13 |
| Glycerol monostearate | 0.25 |
| Fragrance | 0.25 |
| Citric acid | 0.09 |
| Kathon CG[3] | 0.04 |
| DRO water | q.s. |

[1]G.E.S.E.76
[2]Offered by Inolex Chemical Division of American Can Co.
[3]Offered by Rohm and Haas Company, Inc.
[4]Weight average molecular weight of from about 75,000 to about 150,000.

EXAMPLES V–VII

The following are hair styling/conditioning rinse compositions representative of the present invention.

| Component | V | VI | VII |
|---|---|---|---|
| Citric Acid | 0.02 | 0.02 | 0.02 |
| Sodium Citrate | 0.09 | 0.09 | 0.09 |
| Cetyl Alcohol | 0.12 | 0.12 | 0.12 |
| Stearyl Alcohol | 0.08 | 0.08 | 0.08 |
| Natrosol Plus CS Grade D-67 [1] | 1.25 | 1.40 | 1.35 |
| Xanthan Gum [2] | 0.25 | 0.25 | 0.25 |
| Styling Polymer Premix | | | |
| Styling Polymer [3] | 1.75 | 1.15 | 1.75 |
| Octamethyl Tetrasiloxane | 6.89 | 6.89 | 6.89 |

-continued

| Component | V | VI | VII |
|---|---|---|---|
| Diisopropyl adipate | 2.30 | 2.30 | 2.30 |
| Butyl Stearate | 0.15 | — | — |
| Kathon CG | 0.03 | 0.03 | 0.03 |
| Perfume | 0.33 | 0.33 | 0.33 |
| Thickener Premix | | | |
| Water | 11.67 | 11.90 | 12.48 |
| Adogen 470 | 0.67 | 1.33 | — |
| Ditallow dimethyl ammonium chloride | — | — | 0.75 |
| Kemamine ® BQ-2802C | 0.33 | — | — |
| Silicone Gum Premix | | | |
| Decamethyl Pentasiloxane | 1.98 | 1.42 | 1.42 |
| Polydimethyl Siloxane Gum [4] | 0.35 | 0.25 | 0.25 |
| Amodimethicone (Dow Corning Q2-8220) | — | 0.10 | 0.10 |
| Water | q.s | q.s | q.s |

[1] Hydrophobically modified hydroxyethyl cellulose from Aqualon Corp.
[2] Readily dispersible xanthan gum
[3] t-butylacrylate homopolymer, having a weight average molecular weight of about 95,000.
[4] SE-76 gum available from General Electric The styling polymer premix is prepared by combining the styling polymer, the octamethyl tetrasiloxane and decamethyl pentasiloxane and butyl stearate.

The silicone gum premix is prepared by combining and mixing (in a separate vessel) the silicone gum and decamethyl pentasiloxane until homogeneous.

The thickener premix is prepared by combining and mixing (in a separate vessel) water, any primary and secondary thickeners (premelted), the silicone gum premix, and any other optional silicones, at 71° C., until homogeneous.

In another vessel, the water is heated to 71° C. Citric acid, sodium citrate, cetyl alcohol, stearyl alcohol and Natrosol Plus CS grade D-67 are added an mixed till homogeneous. The xanthan gum is added and mixed till homogeneous. The styling polymer premix, Kathon CG and perfume are added and mixed till homogeneous. The composition is further dispersed with an in-line homogenizer (such as a Tekmar homogenizer) and then cooled to 38° C.

The thickener premix is also further dispersed with an in-line homogenizer and cooled to 38° C. and added to the final vessel, mixing until homogeneous to form the styling rinse composition.

What is claimed is:

1. A hair styling composition comprising:
   (a) from about 0.1% to about 50%, by weight, of a hair styling agent, said hair styling agent comprising:
      (i) a hair styling polymer consisting essentially of hydrophobic monomers, wherein said hydrophobic monomers are t-butylacrylate, said polymer having a weight average molecular weight of at least about 10,000 and a solubility in water at 25° C. of about 0.1% or less, calculated on a water plus polymer weight basis; and
      (ii) a water-insoluble volatile diluent for said hair styling polymer, said diluent selected from the group consisting of hydrocarbons, esters, ethers, alkyl alcohols, silicones, and mixtures thereof, and having a boiling point, at atmospheric pressure, of from about 100° C. to about 300° C. and a solubility in water at 25° C. of 0.2% or less, calculated on a water plus diluent weight basis; wherein the weight ratio of said hair styling polymer to said volatile diluent is from about 1:100 to about 5:1; and
   (b) an aqueous carrier wherein the composition provides hair styling performance without causing the hair to become excessively sticky or stiff.

2. A hair styling composition as in claim 1, wherein said weight average molecular weight is at least about 30,000.

3. A hair styling composition as in claim 2, wherein said weight average molecular weight is at least about 50,000.

4. A hair styling composition as in claim 3, wherein said weight average molecular weight is at least about 75,000.

5. A hair styling composition as in claim 3, wherein said weight average molecular weight is from about 50,000 to about 200,000.

6. A hair styling composition as in claim 1, wherein said diluent is diisopropyl adipate.

7. A hair styling composition as in claim 6, wherein said diluent is a mixture of diisopropyl adipate and volatile silicone, and said weight average molecular weight is from about 75,000 to about 150,000.

8. A hair styling composition as in claim 1, wherein said aqueous carrier comprises a combination of a lipid vehicle material and a cationic surfactant, or a hydrophobically modified nonionic water-soluble polymer and a thickening material for said hydrophobically modified, nonionic water-soluble polymer, or a mixture thereof.

9. A hair styling composition as in claim 1, wherein said aqueous carrier comprises a combination of a lipid vehicle material and a cationic surfactant, or a hydrophobically modified nonionic water-soluble polymer and a thickening material for said hydrophobically modified, nonionic water-soluble polymer, or a mixture thereof.

10. A hair care composition as in claim 8, wherein said aqueous carrier comprises a water-soluble polymer which is a cellulose ether.

11. A hair care composition as in claim 9, wherein said aqueous carrier comprises a water-soluble polymer which is a cellulose ether.

12. A hair styling composition as in claim 1, further comprising a hair conditioning agent.

13. A hair styling composition, as in claim 12, wherein said hair conditioning agent comprises a cationic surfactant or a nonvolatile silicone, or a mixture thereof.

14. A hair styling composition as in claim 8, further comprising a nonvolatile silicone hair conditioning agent.

15. A method for styling hair comprising applying an effective amount to provide styling hold of the composition of claim 1 to the hair, and then drying and styling the hair.

16. A method for styling and conditioning hair comprising applying an effective amount of the composition of claim 12 to the hair, and then drying and styling the hair.

17. A method for styling and conditioning hair comprising applying an effective amount of the composition of claim 8 to wet hair, rinsing the hair, and then drying and styling the hair.

* * * * *